United States Patent
Fuhr et al.

(10) Patent No.: US 10,537,508 B2
(45) Date of Patent: Jan. 21, 2020

(54) CONDITIONING SHAMPOO WITH ESTER MIXTURES OF PLANT OILS

(71) Applicant: Henkel AG & Co. KGaA, Duesseldorf (DE)

(72) Inventors: Denise Fuhr, Schenefeld (DE); Dirk Hentrich, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/753,921

(22) PCT Filed: Jul. 27, 2016

(86) PCT No.: PCT/EP2016/067863
§ 371 (c)(1),
(2) Date: Feb. 20, 2018

(87) PCT Pub. No.: WO2017/029085
PCT Pub. Date: Feb. 23, 2017

(65) Prior Publication Data
US 2018/0250211 A1    Sep. 6, 2018

(30) Foreign Application Priority Data
Aug. 20, 2015 (DE) .................. 10 2015 215 860

(51) Int. Cl.
| A61K 8/39 | (2006.01) |
| A61Q 5/02 | (2006.01) |
| A61Q 5/12 | (2006.01) |
| A61K 8/34 | (2006.01) |
| A61K 8/37 | (2006.01) |
| A61K 8/92 | (2006.01) |

(52) U.S. Cl.
CPC ............. *A61K 8/39* (2013.01); *A61K 8/345* (2013.01); *A61K 8/37* (2013.01); *A61K 8/922* (2013.01); *A61Q 5/02* (2013.01); *A61Q 5/12* (2013.01); *A61K 2800/34* (2013.01); *A61K 2800/591* (2013.01); *A61K 2800/596* (2013.01)

(58) Field of Classification Search
None
See application file for complete search history.

(56) References Cited

U.S. PATENT DOCUMENTS 5,747,436 A * 5/1998 Patel .................. A61K 8/39
510/124

FOREIGN PATENT DOCUMENTS

| EP | 1518537 A2 | 3/2005 | |
| EP | 2532689 A1 | 12/2012 | |
| WO | 9308787 A2 | 5/1993 | |
| WO | 2005030163 A1 | 4/2005 | |
| WO | 2015086006 A1 | 6/2015 | |
| WO | WO 2015/086006 * | 6/2015 | ............ A61Q 5/02 |

OTHER PUBLICATIONS

Burnett et al., Int. J. Toxicol., 2014, 33(S4), pp. 13S-39S. (Year: 2014).*
Jang et al., Toxicol. Res., 2015, 31(2), pp. 105-136. (Year: 2015).*
EPO, International Search Report and Written Opinion issued in International Application No. PCT/EP2016/067863, dated Jul. 27, 2016.

* cited by examiner

*Primary Examiner* — Brian Gulledge
(74) *Attorney, Agent, or Firm* — Lorenz & Kopf, LLP

(57) ABSTRACT

Subject matter of the present disclosure is a conditioning shampoo containing (A) a mixture of the mono-, di- and tri-esters of a fatty acid mixture (F1) and glycerine, and (B) a mixture of the mono- and di-esters of a fatty acid mixture (F1) and a polyethylene glycol having a mean molecular mass of from 200 to 800 g/mol, wherein the fatty acid mixture (F1) is a mixture of fatty acids which has the same fatty acid composition as a plant-based oil, and, relative to the total weight of the shampoo, the total quantity of all the plant-based oils included in the shampoo, which are not the same as the tri-esters of the fatty acid mixture (F1) and glycerine, is a value of maximum 0.25 wt. %, and the total quantity of all the silicone compounds included in the shampoo is a value of maximum 0.25 wt. %.

17 Claims, No Drawings

CONDITIONING SHAMPOO WITH ESTER MIXTURES OF PLANT OILS

TECHNICAL FIELD

This application is a U.S. National-Stage entry under 35 U.S.C. 371 based on International Application No. PCT/EP2016/067863, filed Jul. 27, 2016, which was published under PCT Article 21(2) and which claims priority to German Application No. 10 2015 860.8, filed Aug. 20, 2015, which are all hereby incorporated in their entirety by reference.

The present disclosure concerns the art of cosmetics and relates to conditioning hair cleansing agents, which contains a mixture of the mono-, di- and triglycerides in a particular fatty acid mixture and glycerine, as well as a mixture of the mono- and diesters of said fatty acid mixture and a polyethylene glycol. The hair cleansing agents are also exemplified in that they contain only very small quantities of other plant-based oils and silicone oils and may dispense with the use thereof.

Cleansing agents (hair shampoos) can be used to cleanse human hair and the scalp and remove sebum, styling agent residues and other contaminants. Due to the tensides (mostly anionic) usually contained in hair cleansing agents, hair cleansing always involves the removal of lipids and proteins from the hair or the scalp, wherein damage to the hair structure and/or a drying of the scalp can occur, more particularly in case of frequent cleansing.

Damage to the hair structure of the hair fibers, more particularly split ends and/or hair break, can also be encouraged by environmental influences, such as intense solar irradiation), mechanical loads (such as combing under the heat of a hair dryer), as well as by chemical influences (such as coloring, deforming or straightening the hair).

To prevent and/or minimize hair damage, various nourishing agents, such as cationic nourishing polymers, oils and/or silicone compounds have, in the past, been added to hair shampoos.

All these nourishing agents are able to achieve a nourishing effect and/or a conditioning effect, which manifests itself, for example, in improved hold or improved combability of the hair. At the same time, however, the use of the aforementioned nourishing agents can have various disadvantages, which are negatively perceived by the consumer and which can deter him/her from repeated use of the shampoo.

For example, although the use of larger oil quantities in shampoos improves combability, oils also burden the hair and leave a greasy film. Repeated use in particular can cause an accumulation of said effect, and therefore the hair appears unkempt and unattractive, even immediately after being washed and dried.

The use of cationic tensides and cationic polymers can lead to electrostatic charging and cause the hair to "fly away". This effect, too, is increased by repeated use.

Moreover, silicones are known for their nourishing effect. WO 93/08787 A1, for example, relates to the production of hair nourishing shampoos containing anionic tensides, cationic polymers, a silicone and a further oil. The use of such shampoos lends the hair more gloss, improved combability and a softer hold. The regular use of nourishing shampoos of this type can, however, as described above, lead to an "over-nourishing" (so-called build-up effect) of the hair. In addition to the aforementioned greasy hair feel, this includes above all a low hair volume and/or a lank, unkempt appearance of the hair. Build-up effects occur particularly frequently on fine and/or damaged hair, and more particularly after the repeated use of nourishing shampoos containing silicones, oils and cationic polysaccharide polymers.

The consumer is well aware of the negative effects of said nourishing agents. Some consumers perceive the silicones, in addition to oils, in particular in a poor light. Therefore, many consumers are seeking shampoos that are free from silicones and/or oils. However, the chemical name and/or the INCI makes it difficult for consumers not skilled in the art of chemistry to identify the ingredients of the shampoo. Consequently, the consumer seeks a simple and quick way of being able to select a silicone-free and/or oil-free shampoo from the range on offer.

Lipophilic nourishing oils and silicones have to be stabilized through the use of emulsifiers in the formulation, and therefore such shampoos usually exist in a milky white, non-transparent emulsion. If the nourishing shampoo exists in a transparent form, as a gel for example, it is easy for the consumer to acknowledge that this nourishing shampoo is not an emulsion and consequently contains no fatty substances that burden the hair.

Although transparent shampoo formulations containing no lipophilic oils or silicones are known from the prior art in principle, such shampoos are simply cleansing shampoos, not shampoos with a conditioning effect.

The present disclosure therefore addressed the problem of preparing a hair cleansing agent with a high nourishing effect, which does not burden the hair or lead to over-nourishing. To prevent over-nourishing, the nourishing effect of the shampoo is supposed to be achieved without the use of silicones and high quantities of oil. Moreover, the shampoo is supposed to offer the consumer a simple and quick way of establishing that no silicones/oils are contained therein.

BRIEF SUMMARY

In an exemplary embodiment, a conditioning shampoo is provided and includes (A) a mixture of the mono-, di- and tri-esters of a fatty acid mixture (F1) and glycerine. Further, the conditioning shampoo includes (B) a mixture of the mono- and di-esters of a fatty acid mixture (F1) and a polyethylene glycol having a mean molecular mass of from 200 to 800 g/mol. In the conditioning shampoo, the fatty acid mixture (F1) is a mixture of fatty acids which has the same fatty acid composition as a plant-based oil, and, relative to the total weight of the shampoo, the total quantity of all the plant-based oils included in the shampoo, which are not the same as the tri-esters of the fatty acid mixture (F1) and glycerine, is a value of maximum 0.25 wt. %, and the total quantity of all the silicone compounds included in the shampoo is a value of maximum 0.25 wt. %.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now unexpectedly emerged that the aforementioned problems can be solved in an outstanding manner by employing hair cleansing agents which, in addition to the mono-, di- and triglycerides of a specific fatty acid mixture and glycerine, also contain a mixture of the mono- and diesters of said fatty acid mixture and a polyethylene glycol.

Despite their lack of silicones and high quantities of oils, said hair cleaning agents achieve a very high nourishing effect. More particularly, such conditioning shampoos are able to improve hold and combability. No over-nourishing and/or a negative build-up effect occur after repeated use of said shampoo.

Finally, such shampoos can be produced as a clear formulation, i.e. it has been possible to develop a transparent conditioning shampoo, which enables the consumer to establish the absence of lipophilic ingredients which burden the hair simply through a quick visual assessment.

A first subject matter of the present disclosure is therefore a conditioning shampoo containing
(A) a mixture of the mono-, di- and tri-esters of a fatty acid mixture (F1) and glycerine, and
(B) a mixture of the mono- and di-esters of a fatty acid mixture (F1) and a polyethylene glycol having a mean molecular mass of from 200 to 800 g/mol,
wherein
the fatty acid mixture (F1) is a mixture of fatty acids which has the same fatty acid composition as a plant-based oil, and—relative to the total weight of the shampoo—
the total quantity of all the plant-based oils contained in the shampoo, which are not the same as the tri-esters of the fatty acid mixture (F1) and glycerine, is a value of maximum 0.25 wt. %, and
the total quantity of all the silicone compounds contained in the shampoo is a value of maximum 0.25 wt. %.

A shampoo as contemplated herein is a hair cleansing agent containing, in a hydrous or hydrous/alcoholic carrier, at least one tenside, such as at least one anionic and/or amphoteric and/or zwitterionic tenside.

A conditioning shampoo is a hair cleansing agent, which cleans and nourishes the hair at the same time. The conditioning effect and/or nourishing effect may manifest themselves in an improved hold feel and improved combability of the hair.

In other words, the first subject matter of the present disclosure is a conditioning shampoo containing, in a cosmetic carrier, at least one tenside, as well as
(A) a mixture of the mono-, di- and tri-esters of a fatty acid mixture (F1) and glycerine, and
(B) a mixture of the mono- and di-esters of a fatty acid mixture (F1) and a polyethylene glycol having a mean molecular mass of from 200 to 800 g/mol,
wherein
the fatty acid mixture (F1) is a mixture of fatty acids which has the same fatty acid composition as a plant-based oil, and—relative to the total weight of the shampoo—
the total quantity of all the plant-based oils contained in the shampoo, which are not the same as the tri-esters of the fatty acid mixture (F1) and glycerine, is a value of maximum 0.25 wt. %, and
the total quantity of all the silicone compounds contained in the shampoo is a value of maximum 0.25 wt. %.

Tensides are substances that reduce the surface tension of a liquid or the interface tension between two phases. Tensides usually contain a hydrophobic hydrocarbon radical (for example, a hydrocarbon radical having from 8 to 30 carbon atoms), and one hydrophilic molecular fragment.

Anionic tensides are the most frequently used tensides in cosmetic cleansing agents, since they have outstanding foaming power and an excellent cleansing effect.

Suitable anionic tensides, which can be used in the shampoo as contemplated herein, include:
linear and branched fatty acids having from 8 to 30 carbon atoms (soaps),
ether carboxylic acids having the formula R—O—$(CH_2$—$CH_2O)_x$—$CH_2$—COOH, wherein R is a linear or branched, saturated or unsaturated alkyl group having from 8 to 30 carbon atoms and x=0 or from 1 to 16,
acyl sarcosides having from 8 to 24 carbon atoms in the acyl group,
acyl tauride having from 8 to 24 carbon atoms in the acyl group,
acyl isethionates having from 8 to 24 carbon atoms in the acyl group,
sulfosuccinic acid mono- and/or dialkyl esters having from 8 to 24 carbon atoms in the alkyl group and sulfusuccinic acid monoalkyl polyoxyethyl esters having from 8 to 24 carbon atoms in the alkyl group and 1 to 6 oxyethyl groups,
alpha olefin sulfonates having from 8 to 24 carbon atoms,
alkyl sulfate- and/or alkylpolyglycol ether sulfate salts of formula R—$(OCH_2$—$CH_2)_x$—$OSO_3^-X^+$, wherein R is a linear or branched, saturated or unsaturated alkyl group having from 8 to 30 carbon atoms, x=0 or from 1 to 12 and X is an alkali- or ammonium ion,
sulfonates of unsaturated fatty acids having from 8 to 24 carbon atoms and from 1 to 6 double bonds,
esters of tartaric acid and citric acid having alcohols, which are the addition products of from about 2-15 molecules of ethyl oxide and/or propylene oxide on fatty alcohols having from 8 to 22 carbon atoms,
alkyl- and/or alkenyl ether phosphates of the formula,

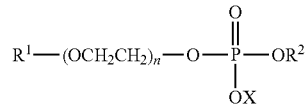

wherein $R^1$ denotes an aliphatic hydrocarbon radical having from 8 to 30 carbon atoms, $R^2$ denotes hydrogen, a radical $(CH_2CH_2O)_n R^1$ or X, n denotes numbers from 0 to 10 and X denotes hydrogen, an alkali or alkaline earth metal or $NR^3R^4R^5R^6$, where $R^3$ to $R^6$ denote a $C_1$ to $C_4$ hydrocarbon radical independently of one other.

Exemplary anionic tensides are ether carboxylic acids with the aforementioned formula, acyl sarcosides having from 8 to 24 carbon atoms in the acyl group, sulfosuccinic acid mono- and/or dialkyl esters having from 8 to 24 carbon atoms in the alkyl group and sulfusuccinic acid mono-alkyl polyoxyethyl esters having from 8 to 24 carbon atoms in the alkyl group and from 1 to 6 oxyethyl groups, alpha olefin sulfonates having from 8 to 24 carbon atoms and/or alkyl sulfate- and/or alkylpolyglycol ether sulfate salts of the aforementioned formula.

Exemplary anionic tensides are straight-chained or branched alkyl ether sulfates containing an alkyl radical having from 8 to 18, such as from 10 to 16 carbon atoms, for example from 1 to 6, such as from 2 to 4 ethylene oxide units. Other exemplary anionic tensides are straight-chained or branched alkyl sulfonates containing an alkyl radical having from 8 to 18, such as from 10 to 16 carbon atoms. In exemplary embodiments, the sodium, magnesium and/or triethanolamine salts are linear or branched lauryl-, tridecyl- and/or myristyl sulfates having a degree of ethoxylation of from 2 to 4.

Further, certain cosmetic agents as contemplated herein are exemplified in that they contain at least one anionic tenside from the group of alkyl sulfates and alkylpolyglycol ether sulfates of formula R—O—(CH$_2$—CH$_2$O)$_n$—O—SO$_3$X, wherein R denotes a straight-chained or branched, saturated or a mono- and/or poly-unsaturated alkyl- or alkenly radical having from 8 to 24 carbon atoms, n denotes from 0 or from 1 to 12 and X denotes an alkali or earth alkali metal or triethanolamine. Exemplary anionic tensides have the INCI trade name sodium lauryl sulfate.

The cosmetic carrier may be a suitable hydrous, alcoholic or hydrous-alcoholic carrier.

An exemplary cosmetic carrier contains at least 50 wt. %, such as at least 60 wt. %, for example at least 65 wt. %, such as at least 70 wt. % water. Furthermore, the cosmetic carrier can contain from 0.01 to 30 wt. %, such as from 0.05 to 20 wt. %, for example from 0.1 to 10 wt. % of at least one alcohol, which is not the same as b). Suitable alcohols include ethanol, ethyldiglycol, 1-propanol, 2-propanol, isopropanol, 1,2-propylene glycol, 1,3-propylene glycol, glycerine, diglycerine, triglycerine, 1-butanol, 2-butanol, 1,2-butandiol, 1,3-butandiol, 1,4-butandiol, 1-pentanol, 2-pentanol, 1,2-pentandiol, 1,5-pentandiol, 1, hexanol, 2-hexanol, 1,2-hexandiol, 1,6-hexandiol, polyethylene glycols, sorbitol, sorbitan, benzyl alcohol, phenoxyethanol or the mixtures thereof.

Exemplary alcohols are water-soluble alcohols, such as ethanol, 1,2-propylene glycol, glycerine, benzyl alcohol and/or phenoxyethanol, as well as the mixtures thereof.

In certain embodiments, as a first component essential to the present disclosure (A), the conditioning shampoos as contemplated herein contain a mixture of the mono-, di- and tri-esters of a fatty acid mixture (F1) and glycerine.

An exemplary fatty acid mixture (F1) is a mixture of two or more linear, branched, saturated or unsaturated $C_8$-$C_{30}$ alkanoic acids or $C_8$-$C_{30}$ alkenoic acids. If one or more fatty acids from the fatty acid mixture (F1) are unsaturated, they can be mono- or poly-unsaturated.

An exemplary fatty acid mixture (F1) is a mixture of at least two fatty acids selected from the group of dodecan acid (lauric acid), tetradecan acid (myristine acid), hexadecanic acid (palmitic acid), tetracosanic acid (lignoceric acid), octadecanic acid (stearic acid), eicosanic acid (arachidic acid), docosanic acid (behenic acid), petroselin acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], eruca acid [(13Z)-docos-13-enic acid], linoleic acid [(9Z,12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-tetracos-15-enic acid].

The mixture (A) from the mono-, di- and tri-esters from the fatty acid mixture (F1) and glycerine is a mixture of the compounds from groups (A1), (A2) and (A3)

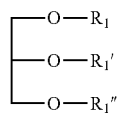
(A1)

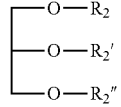
(A2)

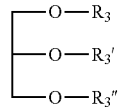
(A3)

wherein in each of the compounds from the group (A1), the radicals R1, R1' and R1" denote, independently of one another, a linear, saturated or mono- or poly-unsaturated $C_8$-$C_{30}$-acyl group, and in each of the compounds from the group (A2), one of the radicals from R2, R2' and R2" denotes a hydrogen atom and the other two radicals denote, independently of one another, a linear, saturated or mono- or poly-unsaturated $C_8$-$C_{30}$-acyl group, and in each of the compounds from the group (A3), two of the radicals from R3, R3' and R3" denotes a hydrogen atom and the third radical denotes a linear, saturated or mono- or poly-unsaturated $C_8$-$C_{30}$-acyl group.

Each $C_8$-$C_{30}$ acyl group corresponds to the relevant fatty acid. If the fatty acid mixture (F1) comprises dodecan acid (lauric acid, $C_{12}H_{24}O_2$), for example, the corresponding $C_8$-$C_{30}$ acyl group is the group —C(O)—$C_{11}H_{23}$.

Thus, the shampoo as contemplated herein contains a mixture of one or more compounds from the group (A1), additionally a mixture of one or more compounds from the group (A2) and additionally a mixture of at least two compounds from the group (A3).

The sum total of all the compounds from the group (A1) contained in the agent corresponds to the triesters of the fatty acid mixture (F1) and glycerine, i.e. the sum total of all radicals R1, R1' and R1" denotes the acyl radical, which are the structural part of the triester from the fatty acid mixture (F1) and glycerine.

The sum total of all the compounds from the group (A2) contained in the agent corresponds to the diesters of the fatty acid mixture (F1) and glycerine, i.e. the sum total of all radicals R2, R2' and R2' denotes hydrogen, and the remaining ⅔ of all radicals R2, R2' and R2" denote the acyl radicals, which are the structural part of the diester from the fatty acid mixture (F1) and glycerine.

The sum total of all the compounds from the group (A3) contained in the agent corresponds to the monoesters of the fatty acid mixture (F1) and glycerine, i.e. the two thirds of the sum total of all radicals R3, R3' and R3" denotes hydrogen, and the remaining ⅓ of all radicals R3, R3' and R3" denote the acyl radicals, which are the structural part of the diester from the fatty acid mixture (F1) and glycerine.

In each of the compounds of the group (A1), the radicals R1, R1' and R1" can be selected, independently of the radicals of the other representatives, from the group (A1).

In each of the compounds of the group (A2), the radicals R2, R2' and R2" can be selected, independently of the radicals of the other representatives, from the group (A2).

In each of the compounds of the group (A3), the radicals R3, R3' and R3" can be selected, independently of the radicals of the other representatives, from the group (A3).

In an exemplary embodiment, the conditioning shampoo as contemplated herein is exemplified in that the mixture (A) of the mono-, di- and tri-esters of the fatty acid mixture (F1) and glycerine is a mixture of the compounds from the groups (A1), (A2) and (A3),

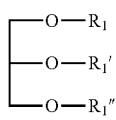 (A1)

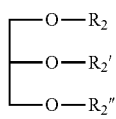 (A2)

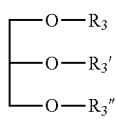 (A3)

wherein
in each of the compounds of the group (A1), the radicals R1, R1' and R1" denote, independently of one another, a linear, saturated or mono- or poly-unsaturated $C_8$-$C_{30}$-acyl group, and in each of the compounds from the group (A2), one of the radicals from R2, R2' and R2" denotes a hydrogen atom and the other two radicals denote, independently of one another, a linear, saturated or mono- or poly-unsaturated $C_8$-$C_{30}$-acyl group, and in each of the compounds from the group (A3), two of the radicals from R3, R3' and R3" denotes a hydrogen atom and the third radical denotes a linear, saturated or mono- or poly-unsaturated $C_8$-$C_{30}$-acyl group.

The fatty acid mixture (F1) is a mixture of at least two different—such as three different—fatty acids.

As a triester with glycerine, this fatty acid mixture forms the compounds from the group (A1).

In principle, the conditioning shampoo can therefore contain only one compound from the group (A1), wherein, however, at least two of the radicals from the group R1, R1' and R1" cannot have the same structure. However, an exemplary conditioning shampoo contains at least two structurally different compounds from the group (A1).

In principle, the conditioning shampoo can also contain only one compound from the group (A2), wherein, however, the two radicals from the group R2, R2' and R2", which do not constitute a hydrogen atom, cannot have the same structure. However, an exemplary conditioning shampoo contains at least two structurally different compounds from the group (A2).

Moreover, the conditioning shampoo contains at least two structurally different compounds from the group (A3).

As a second component essential to the present disclosure (B), the conditioning shampoo contains a mixture of the mono- and di-esters of a fatty acid mixture (F1) and a polyethylene glycol having a mean molecular mass of from 200 to 800 g/mol, The fatty acid mixture (F1) of the component (B) corresponds to the fatty acid mixture (F1) of the component (A).

Therefore, if all esters of the component (A) were to be completely split and all esters of component (B) were to be completely split, the two fatty acid mixtures resulting from the saponification of components (A) and (B) would have this same composition (F1).

The component (B) constitutes a mixture of the mono- and di-esters of the fatty acid mixture (F1) and a polyethylene glycol having a mean molecular mass of from 200 to 800 g/mol.

A polyethylene glycol having a molecular mass of from 200 g/mol to 800 g/mol is a mixture of compounds from the group H—(O—$CH_2$—$CH_2$)$_n$—OH, wherein n, for example, can denote an integer from 1 to 100, and wherein n preferably denotes an integer from 1 to 50, such as from 2 to 40, for example from 3 to 30, such as from 4 to 20. On average, the molecular mass of this mixture is in the range from 200 to 800 g/mol.

Each of the polyethylene glycols from the mixture used has—depending on the integer n—a specific molecular mass. The polyethylene glycol mixture is exemplified by its mean molecular mass.

The molecular mass (alternatively: the molecular weight) is defined as the mass per amount of substance (unit: g/mol). The mean molecular mass (alternatively: the mean molecular weight) of the polyethylene glycol mixture is derived from the total mass of the mixture (i.e. the sum total of the masses of all polyethylene glycols), which is set relative to the total amount of substance in the mixture (i.e. the total quantity of all polyethylene glycols present in the mixture).

Mean molecular mass=total mass (*t* total)/total amount of substance (mol total)

In the case of polymers, the mean molecular mass is a parameter of molecular mass distribution, wherein the molecular mass of all chain lengths is averaged. The expression mean molecular mass used as contemplated herein is alternatively described as a numerical mean of the molecular mass. The mean molecular mass (alternatively: the mean molecular weight) of the polyethylene glycol mixture can, for example, be determined by employing gel permeation chromatography (GPC) with polystyrene as an internal standard according to DIN 55672-3.

The mixture (B) from the mono- and di-esters from the fatty acid mixture (F1) and a polyethylene glycol having a mean molecular mass of from 200 to 800 g/mol is a mixture of the compounds from groups (B1) and (B2)

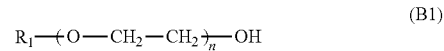 (B1)

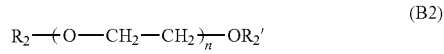 (B2)

wherein
in each of the compounds from the group (B1), the radical R1 denotes a linear, saturated or mono- or poly-unsaturated $C_8$-$C_{30}$-acyl group, and in each of the compounds from the group (B1), the radicals R2, R2' denote, independently of one another, a linear, saturated or mono- or poly-unsaturated $C_8$-$C_{30}$-acyl group, and in each of the compounds from the groups (B1) and (B2), n independently denotes an integer from 1 to 50, such as from 2 to 40, for example from 3 to 30, such as from 4 to 20. As described above, the mean molecular weight of the used polyethylene glycols is required to have a mean molecular mass of from 200 to 800 g/mol.

In each of the compounds of the group (B1), the radicals R1 and n can be selected, independently of the radicals R1 and n of the other representatives, from the group (B1).

In each of the compounds of the group (B2), the radicals R2, R2' and n' can be selected, likewise independently of the radicals of the other representatives R, R2# and n, from the group (B1).

In another embodiment, the conditioning shampoo as contemplated herein is exemplified in that the mixture (B) of the mono- and di-esters of the fatty acid mixture (F1) and a polyethylene glycol having a mean molecular mass of from 200 to 800 g/mol is a mixture of the compounds from the groups (B1) and (B3),

(B1)

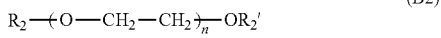
(B2)

wherein
in each of the compounds from the group (B1), the radical R1 denotes a linear, saturated or mono- or poly-unsaturated $C_8$-$C_{30}$-acyl group, and
in each of the compounds from the group (B1), the radicals R2, R2' denote, independently of one another, a linear, saturated or mono- or poly-unsaturated $C_8$-$C_{30}$-acyl group, and
in each of the compounds from the groups (B1) and (B2), n independently denotes an integer from 5 to 12, such as from 6 to 11, for example from 7 to 10.

The conditioning shampoo as contemplated herein contains a mixture (A), said mixture being of the mono- and di- and tri-esters of a fatty acid mixture (F1) and glycerine. Moreover, a conditioning shampoo as contemplated herein also contains a mixture (B), said mixture being of the mono- and di- and tri-esters of a fatty acid mixture (F1) and a polyethylene glycol having a mean molecular mass of from 200 to 800 g/mol. Both mixtures (A) and (B) are based on the fatty acid mixture (F1).

An essential feature of the fatty acid mixture (F1) is that it constitutes a mixture of fatty acids, which has the same fatty acid composition as a plant-based oil.

Plant-based oils are mixtures of fatty acid triglycerides, which can be obtained by extracting or pressing the seeds, kernels or the pulp of a plant, for example. At room temperature (22° C.) and normal pressure (1 atm and/or 1013 mbar), plant-based oils are waxy to liquid, with an exemplary plant-based oil being liquid.

If said fatty acid triglycerides are split into their component parts—by employing hydrolysis for example, glycerine and the fatty acid mixture characteristic of the plants concerned are obtained.

Shampoos with a particularly effective nourishing effect can be developed by basing mixtures (A) and (B) on a fatty acid mixture (F1), which has the same fatty acid composition as an oil from the group of almond oil, apricot kernel oil, argan oil, avocado oil, babassu oil (Orbignya Oleifera kernel oil), Brazil nut oil (Bertholletia Excelsa kernel oil), bitter cherry kernel oil, grape seed oil, water melon kernel oil, macadamia nut oil (Macadamia Ternifolia kernel oil), marula oil (Sclerocarya Birrea kernel oil), maneketti oil (Schinzipphyton Rautenii kernel oil), sunflower oil, olive oil, dog rose oil (Rosa Rubiginosa kernel oil) or thistle kernel oil.

In another embodiment, the shampoo as contemplated herein is exemplified in that the fatty acid mixture (F1) is a mixture of fatty acids, which has the same fatty acid composition as an oil from the group of almond oil, apricot kernel oil, argan oil, avocado oil, babassu oil (Orbignya Oleifera kernel oil), Brazil nut oil (Bertholletia Excelsa kernel oil), bitter cherry kernel oil, grape seed oil, water melon kernel oil, macadamia nut oil (Macadamia Ternifolia kernel oil), marula oil (Sclerocarya Birrea kernel oil), maneketti oil (Schinzipphyton Rautenii kernel oil), sunflower oil, dog rose oil (Rosa Rubiginosa kernel oil) or thistle kernel oil.

The name almond oil (Prunus amygdalus dulcis (Sweet Almond) Oil) means the plant-based oil, which is obtained from both the sweet (lat. dulcis) and also the bitter (lat. amarus) almonds (by employing cold-pressing. for example). The fatty acid mixture of almond oil typically contains a max. of 0.1 wt. % of saturated fatty acids with a chain length of less than 16 carbon atoms, from 4.0-9.0 wt. % palmitic acid, max. 0.8 wt. % palmitoleic acid, max. 0.2 wt. % margarine acid, max. 3.0 wt. % stearic acid, from 62.0-86.0 wt. % oleic acid, from 20.0-30.0 wt. % linoleic acid, max. 0.4 wt. % linolenic acid, max. 0.2 wt. % arachidic acid, max. 0.3 wt. % eicosenoic acid, max. 0.2 wt. % behenic acid and max. 0.1 wt. % erucic acid.

Apricot oil is a plant-based oil obtained from apricot kernels. The fatty acid mixture of apricot kernel oil typically contains from 65.0-66.0 wt. % oleic acid, from 25.0-26.0 wt. % linoleic acid, from 5.0-6.0 wt. % plamitic acid, from 1.0-2.0 stearic acid and from 0.1-1.0 wt. % palmitoleic acid.

Aran oil (also referred to as arganie oil) is usually obtained from the seeds of the yellow berry fruit of the argan tree (*A. spinosa*) by employing pressing. The fatty acid mixture of argan oil typically contains from 44.0-46.0 wt. % oleic acid, from 33.0-35.0 wt. % linoleic acid, max. 0.5 wt. % linoleic acid, from 14.0-18.0 wt. % palmitic acid, from 5.0-6.0 wt. % stearic acid, max. 0.3 wt. % arachidonic acid, max. 0.4 wt. % gadolenic acid.

Avocado oil is obtained from the pulp of the avocado. The fatty acids in avocado oil usually comprise from 47.0 to 70.0 wt. % oleic acid, from 9.0-15.0 wt. % linoleic acid, from 15.0-23.0 wt. % palmitic acid and from 5.0-13.0 wt. % palmitoleic acid.

Babassu oil (Orbignya Oleifera Kernel oil) is the oil of the seeds of *Orignya oleifera*, also referred to as Babassu Palme. A typical fatty acid mixture of babassu oil usually contains approx. 39.0-41.0 wt. % laurinic acid, approx. 15.0 wt. % myristinic acid, approx. 16.0 wt. % oleic acid, approx. 4.0 wt. % linoleic acid, approx. 4.0 wt. % caprylic acid and approx. 4.0 wt. % caprinic acid.

Brazil nut oil (Bertholletia Excelsa kernel oil) can be obtained from the dried and peeled seeds, normally by employing cold-pressing. Usually, the fatty acid mixture comprises Brazil nut oil from the fatty acids from 14.0-16.0 wt. % palmitic acid, from 6.0-10.0 wt. % stearic acid, from 29.0-48.0 wt. % oleic acid and from 30.0-47.0 linoleic acid.

Grape seed oil is an oil, which is obtained from the kernels of grapes. It can be obtained by employing hot-pressing or cold-pressing. The fatty acid mixture of the grape seed oil typically comprises from 7.4-10.2 wt. % palmitic acid, from 3.0-4.7 wt. % stearic acid, from 16.1-21.6 wt. % oleic acid and from 63.3-71.4 wt. % linoleic acid.

Water melon kernel oil is also referred to as Karingda Oil, Oontanga Oil or Watermelon Seed Oil. Water melon kernel oil usually has a fatty acid composition of from 11.0-19.0 wt. % palmitic acid, from 13.0-17.0 wt. % stearic acid, from 14.0-22.0 wt. % oleic acid and from 52.0-58.0 wt. % linoleic acid.

Macadamia is a plant species in the family of silver tree plants (Proteaceae). It is known above all through the fruit, which is known as the macadamia nut. Oil can be obtained from the macadamia nut by employing cold-pressing, for example. Macadamia nut oil (Macadamia Ternifolia kernel oil) usually has a fatty acid composition of from 0.5-1.5 wt. % myristinic acid, from 8.0-9.0 wt. % palmitic acid, from 2.5-3.5 wt. % stearic acid, from 55.0-58.0 wt. % oleic acid, from 20.0-22.0 wt. % palmitoleic acid and from 1.5-2.5 wt. % linoleic acid.

The marula tree belongs to the Anacardiaceae, the sumach plant family and hence to the same family as mango (*Mangifera indica*), akajou tree (*Anacardium occidentale*, cashew) and pistachio tree (*Pistacia vera*). Its approximately plum-size, yellow stone fruits contain an aromatic, sweet-sour and translucent white pump and a very hard seed with two or more oil-rich kernels (up to 56% oil), from which the marula oil is obtained. The fatty acid mixture of the marula oil (Sclerocarya Birrea kernel oil) usually contains from 65.0-70.0 wt. % oleic acid, from 13.0-15.0 wt. % palmitic acid, from 9.0-11.0 wt. % stearic acid, up to 8.0 wt. % linoleic acid.

Maketti seed oil (Schinzipphyton Rautenii kernel oil) is also referred to as mongongo oil. The oil is obtained from the kernel of the mongongo fruit by employing the standard pressing process.

Sunflower oil usually has a fatty acid composition of max. 0.1 wt. % laurinic acid max. 0.2 wt. % myristinic acid, from 4.0-8.0 wt. % palmitic acid, max. 0.3 wt. % palmitoleic acid, from 3.0-7.0 wt. % stearic acid, from 14.0-39.4 wt. % oleic acid, from 60.0-88.0 wt. % linoleic acid, max. 0.3 wt. % linolenic acid, max. 0.5 wt. % arachidic acid, max. 0.3 wt. % gadoleinic acid and from 0.3-1.5 wt. % behenic acid.

Olive oil is plant-based oil pressed from the pulp and from the kernel of olives. Olive oil usually contains fatty acids as a mixture of from 64.0-68.0 wt. % oleic acid, from 11.0-16.0 wt. % linoleic acid, from 8.0-10.0 wt. % palmitic acid, from 4.0-6.0 wt. % eicosaenic acid and from 4.0-6.0 wt. % palmitoleic acid.

Dog rose oil (Rosa Rubiginosa kernel oil) is obtained from the seeds contained in the dog rose, the fruits of the roses, by employing mechanical pressing or extraction. The fatty acid composition of dog rose oil is on average from 27.0-31.0 wt. % oleic acid, from 55.0-58.0 wt. % linoleic acid, from 8.0-10.0 wt. % linolenic acid, from 2.0-6.0 wt. % palmitic acid and from 1.5-4.0 wt. % stearic acid.

Thistle kernel oil or thistle seed oil typically has a fatty acid composition of from 5.3-8.0 wt. %, palmitic acid, from 1.9-2.9 wt. % stearic acid, from 8.4-21.3 wt. % oleic acid, from 67.8-83.2 wt. % linoleic acid and max. 0.1 wt. % linolenic acid.

Every plant oil is exemplified by its content of various fatty acids within specific quantity ranges. Since plant-based oils are natural ingredients, the specified fatty acid quantities are subject to natural a fluctuation range, which can vary slightly depending on the origin or the oil and the prevailing environmental conditions. The usual quantity ranges are therefore given for all the fatty acids contained in the oil concerned. Of course, all specified weight percentages are added to a maximum of 100 wt. % in each special oil batch.

Within the group of the aforementioned fatty acid mixtures (F1), exemplary mixtures of fatty acids have the same composition of very special plant-based oils. It has emerged as particularly advantageous if the fatty acid mixture (F1) is a mixture of fatty acids with the same fatty acid composition as an oil from the group of apricot kernel oil, argan oil, avocado oil, sunflower oil, in particular sunflower oil. Fatty acid mixtures (F1), which have the same composition as the aforementioned plant-based oils, created—when used in the form of ester mixtures (A) and (B)—a particularly good conditioning effect of the shampoo, which was manifested in a particularly smooth hold and particularly good wet and dry combability.

In another embodiment, the conditioning shampoo as contemplated herein is exemplified in that the fatty acid mixture (F1) is a mixture of fatty acids with the same fatty acid composition as an oil from the group of apricot kernel oil, argan oil, avocado oil, sunflower oil, in particular sunflower oil.

In a certain exemplary embodiment, the conditioning shampoo as contemplated herein is exemplified in that the fatty acid mixture (F1) is a mixture of fatty acids, which has the same fatty acid composition as sunflower oil.

As already described, the fatty acid mixture (F1), which has the same fatty acid composition as sunflower oil, is exemplified by the primary components
from 4.0-8.0 wt. % palmitoleic and
from 3.0-7.0 wt. % stearic acid. and
from 14.0-39.4 wt. % oleic acid and
from 60.0-88.0 wt. % linoleic acid.

In this case too, all the stated weight percentages make up a maximum of 100 wt. %, wherein small quantities of one or more of the other aforementioned fatty acids can also be contained.

In another exemplary embodiment, the conditioning shampoo as contemplated herein is exemplified in that the fatty acid mixture (F1) is a mixture of fatty acids which—relative to the total weight of the fatty acid mixture (F1)—comprises
from 4.0-8.0 wt. % palmitoleic and
from 3.0-7.0 wt. % stearic acid. and
from 14.0-39.4 wt. % oleic acid and
from 60.0-88.0 wt. % linoleic acid.

From this exemplary fatty acid mixture (F1) and glycerine, the mixture (A) is formed from the mono-, di- and tri-esters of said fatty acid mixture (F1) and glycerin by employing esterification with glycerine. In other words, the sum total of all mono-, di- and tri-esters of the mixture (A) contains a fatty acid mixture (F1) with a distribution which—relative to the total weight of the fatty acid mixture—comprises
from 4.0-8.0 wt. % palmitoleic and
from 3.0-7.0 wt. % stearic acid. and
from 14.0-39.4 wt. % oleic acid and
from 60.0-88.0 wt. % linoleic acid From this exemplary fatty acid mixture (F1) and the polyethylene glycols having a mean molecular mass from 200 to 800 g/mol, the mixture of the mono- and di-esters (B) is then formed by employing esterification. In other words, the sum total of all mono- and di-esters of the mixture (B) contains a fatty acid mixture (F1) with a distribution which—relative to the total weight of the fatty acid mixture—comprises
from 4.0-8.0 wt. % palmitoleic and
from 3.0-7.0 wt. % stearic acid. and
from 14.0-39.4 wt. % oleic acid and
from 60.0-88.0 wt. % linoleic acid.

A conditioning shampoo with a particularly clear appearance and good nourishing effect can be obtained if the shampoo contains the mixture of mono-, di- and tri-esters (A) and the mixture of mono- and di-esters (B) within specific quantity ranges.

If the shampoo contains the mixtures (A) and (B)—relative to the total weight of the shampoo—in a total quantity[(A)+(B)] from 0.4 to 3.5 wt. %, such as from 0.5 to 2.5 wt. %, for example from 0.6 to 2.0 wt. %, such as from 0.7 to 1.5 wt. %, for example from 0.8 to 1.4 wt. %, transparent formulations that create a particularly pleasant hold on the shampooed hair can be achieved. Hair treated with said agents are also exemplified by particularly good wet and dry combability. If the mixtures (A) and (B) are used in the shampoo in a total quantity of more than 3.5 wt. %, the conditioning effect runs against a limit value, i.e. the use of even higher total quantities[(A)+(B)] does not further improve the nourishing effect.

In another embodiment, the conditioning shampoo as contemplated herein contains—relative to its total weight—the mixtures (A) and (B) in a total quantity [(A)+(B)] from 0.4 to 3.5 wt. %, such as from 0.5 to 2.5 wt. %, for example from 0.6 to 2.0 wt. %, such as from 0.7 to 1.5 wt. %, for example from 0.8 to 1.4 wt. %.

The mixtures (A) and (B) as contemplated herein are known, for example, under the INCI trade names of Olive oil PEG-8 Ester, apricot kernel oil PEG-8 Ester, argan oil PEG-8 Ester, avocado oil PEG-8 Ester or sunflower oil PEG-8 Ester.

Olive oil PEG-8 Ester can, for example, be obtained by the transesterification of olive oil with PEG-8 (a mixture of polyethylene glycols having a mean molecular weight of 370 g/mol). Olive oil PEG-8 Ester is a raw material containing both the mixture (A) and the mixture (B).

Apricot kernel oil PEG-8 Ester can, for example, be obtained by the transesterification of apricot oil with PEG-8 (a mixture of polyethylene glycols having a mean molecular weight of 370 g/mol). Apricot oil PEG-8 Ester is a raw material containing both the mixture (A) and the mixture (B).

Likewise, argan oil PEG-8 Ester can be obtained by the transesterification of argan oil with PEG-8. Avocado oil PEG-8 Ester can be obtained by the transesterification of avocado oil with PEG-8. Argan oil PEG-8 Ester is a raw material containing both the mixture (A) and the mixture (B).

Sunflower oil PEG-8 Ester can be obtained by the transesterification of sunflower oil with PEG-8. Sunflower oil PEG-8 Ester is a raw material containing both the mixture (A) and the mixture (B).

In another embodiment, the conditioning shampoo as contemplated herein contains the mixtures (A) and (B), which are selected from the group of compounds known under the INCI trade names of apricot kernel oil PEG-8 Ester, argan oil PEG-8 Ester, avocado oil PEG-8 Ester or sunflower oil PEG-8 Ester, in particular sunflower oil PEG-8 Ester.

The conditioning shampoos as contemplated herein are exemplified by their good nourishing effect, wherein they condition the hair without having any burdening effect. Even after repeated use of the shampoo as contemplated herein, no "over-nourishing" occurs, i.e. the user does not notice any oily gloss, no greasy hair feel and no volume decrease, even after repeated shampooing.

In this context, it is essential to the present disclosure that the shampoos, apart from the mixture (A) of the mono-, di- and tri-esters, are substantially free from other plant-based oils. In other words, paramount to avoiding over-nourishing is that the tri-ester of the fatty acid mixture (F1) and glycerine is contained in the shampoo only mixed with the corresponding mono- and di-esters of the same fatty acid mixture, and that no other plant-based oils are added to the shampoo.

Therefore, a feature of the conditioning shampoo essential to the present disclosure is that the total quantity of all plant-based oils contained in the shampoo, which are not the same as the tri-esters of the fatty acid mixture (F1) and glycerine, is a value of maximum 0.25 wt. %. The percentage weight value here refers to the total weight of the shampoo.

As described above, a plant-based oil according to the present disclosure is a mixture of fatty acid triglycerides of plant origin, which is waxy to liquid, in an exemplary embodiment liquid, at room temperature (22° C.) and normal pressure (1 atm and/or 1013 mbar).

If the content of added plant-based oils (i.e. plant-based oils that are not the same as the tri-esters of the fatty acid mixture (F1) and glycerine) is maximum 0.25 wt. %, an over-nourishing of the hair can be avoided. It is also possible to formulate a shampoo with a transparent appearance. In an exemplary embodiment, the content of additional plant-based oils, however, is a value of maximum 0.20 wt. %, such as maximum 0.15 wt. %, for example maximum 0.10 wt. %, such as maximum 0.05 wt. %, wherein all the aforementioned weight percentages refer to the total weight of the shampoo. The smaller the content of additional oils, the better an "over-nourishing" of the hair can be avoided.

In another embodiment, the conditioning shampoo as contemplated herein is exemplified in that—relative to the total weight of the shampoo—the total quantity of all plant-based oils contained in the shampoo, which are not the same as the tri-esters of the fatty acid mixture (F1) and glycerine, is a value of maximum 0.20 wt. %, such as of maximum 0.15 wt. %, for example of maximum 0.10 wt. %, such as of maximum 0.05 wt. %.

It has unexpectedly emerged that the working the mixtures of (A) and (B) into the shampoo achieves an equally good and/or even better conditioning effect. In comparison to shampoos that did not contain the mixtures (A) and (B), but instead the same quantity of a similar plant-based oil, at least an equally good and/or a better conditioning effect was achieved, and a burdening and greasy appearance of the hair avoided.

As an optional component, the shampoo as contemplated herein can in principle contain mineral oils. Mineral oils, paraffin and iso-paraffin oils, as well as synthetic hydrocarbons, for example, are used as mineral oils. An example of a usable hydrocarbon is the commercially available 1,3-Di-(2-ethylhexyl)-cyclohexan (Cetiol® S).

In another embodiment, the conditioning shampoo as contemplated herein is, however, exemplified in that—relative to the total weight of the shampoo—the total quantity of all mineral oils from the group of hydrocarbons contained in the shampoo is a value of maximum 0.25 wt. %, such as of maximum 0.20 wt. %, for example of maximum 0.15 wt. %, such as of maximum 0.05 wt. %.

As another optional component, the shampoo as contemplated herein can also contain further fatty substances. Fatty substances are fatty alcohols, as well as natural and synthetic waxes, which can exist both in solid form and liquid form on hydrous dispersions.

According to this present disclosure, fatty acids are considered anionic tensides rather than fatty substances.

Saturated, mono- or poly-unsaturated, branched or unbranched fatty alcohols with $C_8$-$C_{30}$—, such as $C_{10}$-$C_{22}$, for example $C_{12}$-$C_{22}$ carbon atoms, can be used as fatty alcohols. Decanol, octanol, octenol, dodecenol, decenol, octadienol, dodecadienol, decadienol, oleyl alcohol, eruca alcohol, rcinol alcohol, stearyl alcohol, isostearyl alcohol, cetyl alcohol, lauryl alcohol, myristyl alcohol, arachidyl alcohol, capryl alcohol, caprin alcohol, linoleyl alcohol, linolenyl alcohol and behenyl alcohol, for example, can be used.

In another embodiment, the conditioning shampoo as contemplated herein is, however, exemplified in that—relative to the total weight of the shampoo—the total quantity of all fatty alcohols contained in the shampoo is a value of maximum 0.25 wt. %, such as of maximum 0.20 wt. %, for example of maximum 0.15 wt. %, such as of maximum 0.05 wt. %.

The shampoo as contemplated herein can also contain, in principle, a dialkylether. Usable dialkylethers are particularly di-n-alkylether with a total of between 12 and 36 C-atoms, more particularly 12 to 24 C-atoms, such as for example di-n-octylether, di-n-decylether, di-n-nonylether, di-n-undecylether, di-n-dodecylether, n-hexyl-n-octylether, n-octyl-n-decylether, n-decyl-n-undecylether, n-undecyl-n-dodecylether and n-hexyl-n-undecylether, as well as di-tert.-butylether, di-iso-pentylether, di-3-ethyldecylether, tert.-butyl-n-octylether, iso-pentyl-n-octylether and 2-methylpentyl-n-octylether. An exemplary dialkylether is the commercially available di-n-octylether under the trade name Cetiol® OE.

In another embodiment, the conditioning shampoo as contemplated herein is, however, exemplified in that—relative to the total weight of the shampoo—the total quantity of all di-n-($C_{12}$-$C_{36}$) alkylethers contained in the shampoo is a value of maximum 0.25 wt. %, such as maximum 0.20 wt. %, for example of maximum 0.15 wt. %, such as of maximum 0.05 wt. %.

Conditioning shampoos, which can be formulated without notable quantities of fatty substances, as described above, have the added advantage that they can be produced as a clear, transparent formulation.

Although silicones, like oils, have a conditioning effect, they also burden the hair, often form a shiny film and thereby create the impression of even freshly washed hair having an oily appearance.

Therefore, another feature of the conditioning shampoo which is essential to the present disclosure is that the total quantity of all silicone compounds contained in the shampoo is a value of maximum 0.25 wt. %. The percentage weight value here refers to the total weight of the shampoo.

The term "silicone" refers to a group of synthetic polymers, containing silicon atoms cross-linked via oxygen atoms. Silicones are also referred to as poly(organo)siloxanes. The term "silicone" as used in the present disclosure is any substance, the molecular structure of which comprises at least one silicon atom (Si atom).

If the content of silicones in the conditioning shampoo as contemplated herein is a maximum of 0.25 wt. %, a film formation and an oily hair appearance can be avoided. In exemplary embodiments, however, the total quantity of all silicones contained in the shampoo—relative to the total weight of the shampoo is a value of maximum 0.20 wt. %, such as of maximum 0.15 wt. %, for example a maximum of 0.10 wt. %, such as a maximum of 0.01 wt. %.

In another embodiment, the conditioning shampoo as contemplated herein is exemplified in that—relative to the total weight of the shampoo—the total quantity of all silicone compounds contained in the shampoo is a value of maximum 0.20 wt. %, such as of maximum 0.15 wt. %, for example of maximum 0.10 wt. %, such as of maximum 0.01 wt. %.

Silicones include the following compounds:
(i) Polyalkylsiloxanes, polyarylsiloxanes, polyalkylarylsiloxanes, which are volatile, non-volatile, straight-chained, branched or cyclical, cross-linked or not cross-linked;
(ii) Polysiloxanes, the general structure of which contains one or more organofunctional groups, are selected from:
a) substituted or unsubstituted aminated groups;
b) (Per)fluorinated groups;
c) thiol groups;
d) carboxylate groups;
e) hydroxylated groups;
f) alkoxylated groups;
g) acyloxyalkyl groups;
h) amphoteric groups;
i) bisulfite groups;
j) hydroxyacylamino groups;
k) carboxy groups;
l) sulfonic acid groups; and
m) sulfate or thiosulfate groups;
(iii) linear polysiloxane(A)-polyoxyalkylene(B)-block copolymers of type $(A-B)_n$ where n>3;
(iv) grafted silicone polymers with a non-silicone-containing, organic backbone including an organic main chain, which is formed from organic monomers, which contain no silicone, to which at least one polysiloxane macromer has been grafted within the chain and also, where applicable, to at least one chain end;
(v) grafted silicone polymers with polysiloxane backbone, to which non-silicone-containing, organic monomers have been grafted, which have a polysiloxane main chain, to which at least one organic macromer, which contains no silicone, has been grafted within the chain and also, where applicable, to at least one chain end;
(vi) or the mixtures thereof.

The aforementioned, as well as all other silicones are contained in the shampoo as contemplated herein—relative to the total weight thereof—in a total quantity of maximum 0.25 wt. %.

As a further component, the shampoos as contemplated herein can also optionally contain (C) PEG-40 Hydrogenated Castor Oil. PEG-40 hydrogenated Castor Oil has the CAS No. 61788-85-0 and can be commercially obtained, for example, under the trade name Eumulgin CO 40 (BASF).

PEG-40 Hydrogenated Castor Oil is often used in shampoos as a typical solubilizing agent. Solubilizing agents usually exert a major influence on the viscosity of the shampoo, i.e. the higher the quantity of solubilizing agent contained in the shampoo, the lower the viscosity of the shampoo. In order to work-in and stabilize conventional plant-based oils in shampoos, large quantities of solubilizing agents are usually required.

During the course of the work that led to this present disclosure, it emerged that the mixtures (A) and (B) as contemplated herein can be worked into the shampoo even without large quantities of solubilizing agents.

Unexpectedly, the mixtures (A) and (B) do not influence the viscosity of the shampoo as much as PEG-40 hydrogenated castor oil (C).

For example, the use of components (A), (B) and (C) within their optimally matched quantity ranges, enabled the production of a shampoo, the viscosity of which can be reliably set to the required range, and the viscosity of which remained stable, even over prolonged periods. Particularly stable formulations, the viscosity of which did not change significantly either over extended storage periods or under fluctuating temperatures, can be obtained by selecting as a weight ratio [(A)+(B)]/(C) a value which may be within the range from 6.0 to 16.0, such as from 8.0 to 14.0.

In another embodiment, the conditioning shampoo as contemplated herein additionally contains (C) PEG-40 Hydrogenated Castor Oil, wherein the weight ratio of [(A)+(B)]/(C) is a value from 4.0 to 20.0, such as 6.0 to 16.0, for example from 8.0 to 14.0.

Example: 100 g of a conditioning shampoo contain, in addition to other formulation components,
    1.0 g sunflower oil PEG-8 Ester (mixtures (A) and (B)) and
    0.1 g PEG-40 Hydrogenated Castor Oil
    The weight ratio [(A)+(B)]/(C) is (1.0 g/0.1 g)=10.0.

Use of the mixtures (A) and (B), and also where applicable the PEG-40 Hydrogenated Castor Oils (C) within their optimally matched weight ratios enables the formulation of a shampoo with an optimally set viscosity. There is no need to use any other thickening agents.

More particularly, the use of thickeners from the group of anionic polymers based on (meth)acrylic acids can also be eliminated.

Anionic (meth)acrylic polymers are synthetic polymers, which are obtained through the polymerization or copolymerization of acrylic acids and/or methyacrylic acid monomers.

In another embodiment, the conditioning shampoo as contemplated herein is exemplified in that—relative to its total weight—
the total quantity of all anionic polymers based on (meth) acrylic acid contained in the shampoo is a value of maximum 0.25 wt. %, such as of maximum 0.20 wt. %, for example of maximum 0.10 wt. %, such as of maximum 0.01 wt. %.

Polymers are macromolecules having a molecular weight of at least 1000 g/mol, such as least 2500 g/mol, for example at least 5000 g/mol, which consist of the same, repeating organic units.

Synthetic polymers are produced by polymerization of one monomer type or by polymerization of different, structurally different monomer types. If the polymer is produced by polymerization of one monomer type, it is referred to as a homopolymer. If structurally different monomer types are used in the polymerization process, the resultant polymer is referred to as a copolymer.

The maximum molecular weight of the polymer depends on the degree of polymerization (number of polymerized monomers) and the batch size and is partly determined by the polymerization method. According to the present disclosure, the maximum molecular weight of an exemplary cationic polymer (d) is no more than $10^7$ g/mol, such as no more than. $10^6$ g/mol, for example no more than $10^5$ g/mol.

According to the present disclosure, anionic polymers based on (methy)acrylic acid comprise at least one repeating unit of the formula (PI) and/or at least one structural unit of the formula (PII).

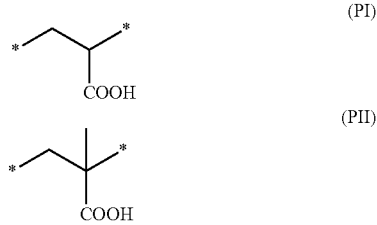

In a hydrous solution, the majority of carboxy groups of the structural units of formula (PI) and/or (PII) exist in deprotonated and hence anionic form.

Polyacrylic and polymethacrylic polymers are cross-linked or non-cross-linked polyacrylic acid and/or polymethacrylic acid polymers, such as those from 3V Sigma, which can be obtained under trade names of Synthalen K or Synthalen M, or from Lubrizol, which can be obtained under the trade names of Carbopol (for example, Carbopol 980, 981, 954, 2984, 5984 and/or Silk 100), each bearing the INCI trade name of Carbomer. The product sold by BASF under the trade name of Cosmedia SP (INCI Name: SODIUM POLYACRYLATE) can also be referred to as a suitable acrylic acid homopolymer in this context.

Copolymer of acrylic acid and/or of methacrylic acid can also be used as polyacrylic and polymethacrylic polymers. A polymer in this context is the polymer known under the INCI trade name of Acrylates/C10-30 Alkyl Acrylate Crosspolymer, which can be obtained under the trade name of Carbopol 1382 from Noveon. Another polymer is the polymer known under the INCI trade name of Acrylates/Steareth-20 Methacrylate Crosspolymer, which is sold, for example, under the trade name of Aculyn® 88 by Rohm & Haas. Other polymers having the INCI nomenclature of Acrylates/Palmeth-25 Acrylate Copolymer or Acrylates/Palmeth-20 Acrylate Copolymer can also be stated. Such polymers can be obtained, for example, under the trade name of Synthalen® W 2000 from 3 V Sigma.

It is also possible to use a copolymer from at least one anionic acrylic acid and/or methacrylic acid monomer and at least one non-ionogenic monomer. Possible non-ionogenic monomers in this context are acrylamide, methacrylamide, acrylic acid ester, methacrylic acid ester, vinylpyrrolidon, vinylether and vinylester.

Other usable polyacrylic and polymethacrylic polymers include copolymers from acrylic acid and/or methacrylic acid or the $C_1$-$C_6$-alkyl esters thereof, as sold under the INCI declaration Acrylates Copolymer. A standard commercial product is, for example, Aculyn® 33 from Rohm & Haas. However, copolymers from acrylic acid and/or methacrylic acid, the $C_1$-$C_6$ alkyl esters of acrylic acid and/or methacacrylic acid, as well as the esters of ethylenically-unsaturated acids and an alkoxylated fatty alcohol. Suitable ethylenically unsaturated acids are, in particular, acrylic acid, methacrylic acid and itaconic acid; suitable alkoxylated fatty alcohols are, in particular, Steareth-20 or Ceteth-20. Such copolymers are sold by Rohm & Haas under the trade name Aculyn® 22 (INCI trade name: Acrylates/Steareth-20 Methacrylate Copolymer).

All these (co)polymers based on (meth)acrylic acid may be used in the shampoo as contemplated herein only in very small quantities and, in certain embodiments, such polymers are not used at all.

Sodium chloride is often used in shampoos as another standard thickener. The use of sodium chloride in the shampoos as contemplated herein can also be drastically reduced and/or avoided through the use of the mixtures (A) and (B) and where applicable (C).

In another embodiment, the conditioning shampoo as contemplated herein is exemplified in that—relative to its total weight—
the total quantity of the sodium chloride contained in the shampoo is a value of maximum 0.25 wt. %, such as of maximum 0.20 wt. %, for example of maximum 0.10 wt. %, such as of maximum 0.01 wt. %.

Polysaccharides are often used in shampoos as other standard thickeners. The use of polysaccharides in the shampoos as contemplated herein can also be drastically reduced and/or avoided through the use of the mixtures (A) and (B) and where applicable (C).

In another embodiment, the conditioning shampoo as contemplated herein is exemplified in that—relative to its total weight—
the total quantity of all anionic and non-ionic polysaccharides contained in the shampoo is a value of maximum 0.25 wt. %, such as of maximum 0.20 wt. %, for example of maximum 0.10 wt. %, such as of maximum 0.01 wt. %.

The pH value of the shampoo as contemplated herein is set to a value within the range from 4.0 to 7.0, such as from 5.3 to 6.7, for example from 5.5 to 6.5, such as from 5.7 to 6.3.

In addition to the aforementioned tensides, the shampoos as contemplated herein can also contain one or more further co-tensides. The selected co-tensides must be mild with strong foaming power, so that they do not negatively influence the foaming properties of the anionic tensides and/or that they increase the foaming properties of the anionic tensides.

Mild amphoteric/zwitterionic and/or mild, non-ionic tensides have proven to be particularly mild co-tensides for the hair cleansing agents as contemplated herein.

Suitable mild amphoteric and/or zwitterionic tensides, which can be used in the hair cleansing agents as contemplated herein include, for example, one or more compounds of the following formulas (I) to (VII), wherein Radical R denotes, in each case, a straight-chained or branched, saturated or mono- or poly-unsaturated alkyl- or alkenyl radical having from 7 to 23 carbon atoms (Formulas (I) and (II)) or a straight-chained or branched, saturated or mono- or poly unsaturated alkyl- or alkenyl radical having from 8 to 24 carbon atoms (Formulas (iii) to (vii)):

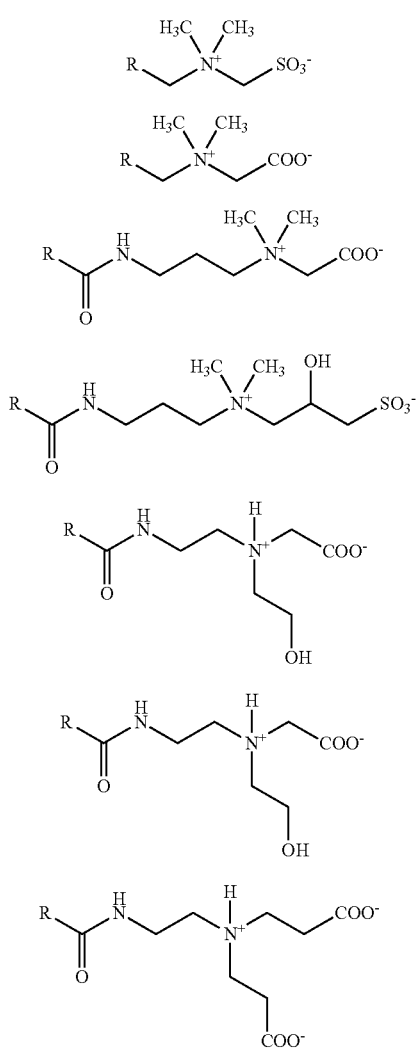

Exemplary amphoteric and/or zwitterionic tensides of one of the above Formulas (I) to (VII) contain primarily as Radical R a straight-chained or branched, saturated, mono- or poly-unsaturated alkyl radical having from 8 to 20, such as from 8 to 18, for example from 8 to 16 carbon atoms.

in exemplary amphoteric and/or zwitterionic tensides, Radical R is derived from coconut oil.

In exemplary embodiments, $C_{10}$-$C_{16}$ alkylampho(di)acetates and/or $C_{10}$-$C_{16}$ alkylamido($C_1$-$C_4$)-alkylbetaines are used with the aforementioned formulas.

Exemplary amphoteric/zwitterionic tensides are known under the INCI trade names of sodium cocoamphoacetate, disodium cocoamphodiacetate, sodium lauroamphoacetate, sodium lauroamphodiacetate, sodium cocoamphopropionate, disodium cocoamphodipropionate, coco betaine, lauryl betaine, cocamidopropylbetain and/or cauramidopropylbetain and are commercially available from several suppliers.

Exemplary tensides have the INCI trade names of Cocamidopropylbetain, Lauramidopropylbetain, Cocoampho(di)acetate and/or Lauroapho(di)acetate.

The percentage weight of the amphoteric and/or zwitterionic tenside relative to the total weight of the cosmetic hair cleansing agent as contemplated herein may be from 0.50 to 15.00 wt. %, such a from 1.00 to 14.00 wt. %, for example from 2.00 to 13.00 wt. %, such as from 2.50 to 12.50 wt. %, for example from 3.00 to 12.00 wt. %.

Suitable non-ionic tensides, which can be used in the cosmetic hair cleansing agents as contemplated herein, include:

addition products of from 4 to 30 moles of ethylene oxide and/or from 0 to 5 moles of propylene oxide on linear fatty alcohols having from 8 to 22 carbon atoms on fatty acids having from 12 to 22 carbon atoms and on alkylphenols having from 8 to 15 carbon atoms in the alkyl group, ethylene oxide and polyglycerine addition products on methylglucoside fatty acid alkanolamides and fatty acid glucamides, aminoxides, sorbitan fatty acid esters and addition products of ethylene oxide onto sorbitan fatty acid esters such as polysorbates, fatty acid alkanolamides of the following general formulas,

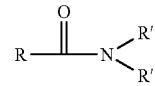

wherein R preferably denotes a linear or branched, saturated or unsaturated alkyl- or alkenyl radical having from 8 to 24 carbon atoms and Radical R' denotes hydrogen or the group —$(CH_2)_n$OH, wherein n denotes the numbers from 2 or 3, provided that one of the radicals R' denotes the aforementioned radical—$(CH_2)_n$OH, sugar fatty acid esters and addition products of ethylene oxide on sugar fatty acid esters, addition products of ethylene oxide on fatty acid alkanolamides and fatty amines and/or alkyl(oligo)glucosides, mixtures of alkyl-(oligo)-glucosides and fatty alcohols, e.g. the product Montanov® 68, Sterine, available in the trade. Sterines refers to a group of steroids, which carry a hydroxyl group on C-Atom 3 of the steroid structure and which are isolated from both animal tissue (zoosterines) and plant-based fats (phytosterines). Examples of zoosterines are cholesterine and lanosterine. Examples of suitable phytosterines are ergosterine, stigmasterine and sitosterine. Sterines, the so-called mykosterines, are also isolated from fungi and yeasts.

Phospholipides. Including primarily the glucose phospolipids, e.g. which are obtained as lecithins and/or phospahtidylcholines from egg yolks or plant seeds (e.g. soja beans).

Suitable alkyl(oligo)glycosides can be selected from compounds of the general formula RO-[G]$_x$, in which [G] is preferably derived from aldose and/or ketose having from 5-6 carbon atoms, such as from glucose.

The index value x denotes the oligomerization degree (DP), i.e. for the distribution of mono and oligoglycosides. In exemplary embodiments, the index value x has a value of from 1 to 10, such as from 1 to 3, wherein said value is not an integer but can be a fraction, which can be determined analytically.

Exemplary alkyl(oligo)glycosides have an oligomerization degree of from 1.2 to 1.5.

An exemplary Radical R denotes at least one alkyl- and/or alkenyl radical having from 4 to 24 carbon atoms.

Exemplary alkyl(oligo)glycosides are the compounds known under the INCI trade names of Caprylyl/Capryl Glucoside, Decyl Glucoside, Lauryl Glucoside and Coco Glucoside.

Suitable amino oxides can be selected from at least one compound of the general formulas (X) or (Y)

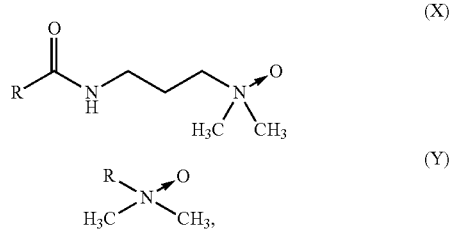

wherein R denotes a straight-chained or branched, saturated or mono- or poly-unsaturated alkyl- or alkenyl radical having from 6 to 24 carbon atoms, such as from 8 to 18 carbon atoms.

Exemplary tensides of the aforementioned formulas (X) or/Y) are known under the INCI trade names of Cocamine Oxide, Lauramine Oxide and/or Cocamidopropylaminoxid and commercially available from various suppliers.

Exemplary non-ionic tensides, which can be contained in the compositions as contemplated herein, are fatty acid alkanolamides, such as the compounds known under the INCI trade names of Cocamide MEA and/or Cocamide MIPA.

Exemplary non-ionic tensides, which can be contained in the compositions as contemplated herein, are also alkyl (oligo)glucosides, such as the compounds known under the INCI trade names of Caprylyl/Capryl Glucoside, Decyl Glucoside, Lauryl Glucoside and/or Coco Glucoside;

In an exemplary embodiment, the percentage weight of the non-ionic tensides relative to the total weight of the cosmetic hair cleansing agent as contemplated herein is from 0.10 to 10.00 wt. %, such as from 0.20 to 8.00 wt. %, for example from 0.30 to 7.00 wt. %, such as from 0.40 to 6.00 wt. %, for example from 0.50 to 5.00 wt. %.

In addition to the aforementioned mandatory and optional active ingredients, the shampoo as contemplated herein can also have one or more other active ingredients, which are selected from the
cationic nourishing polymers
protein hydrolysates and
vitamins.

Protein hydrolysates are product mixtures obtained through the acidically, basically or enzymatically catalyzed decomposition of proteins.

Protein hydrolysates or plant, animal and/or marine origin can be used.

Animal-based protein hydrolysates include elastin-, collagen-, Keratin-, silk- and milk protein hydrolysates, which can also exist in the form of salts. Such products are sold, for example, under the trade names of Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Exemplary protein hydrolysates are of a plant origin, e.g. soja-, almond, rice, pea, potato and wheat protein hydrolysates. Such products can be obtained, for example, under the trade names of Gluadin® (Cognis), DiaMin® (Diamalt), Lexein® (Inolex) and Crotein® (Croda).

Cationic protein hydrolysates can also be used, wherein the basic protein hydrolysate can come from the animal, for example collagen, milk or keratin, from the plant, for example wheat, maize, rice, potatoes, soja or almonds, from marine life forms, such as fish collagen or algae, or from bio-technologically obtained protein hydrolysates. The protein hydrolysates on which the cationic derivatives are based can be obtained from the corresponding proteins by employing a chemical, more particularly alkali or acid hydrolysis, by employing an enzymatic hydrolysis and/or a combination of the two hydrolysis methods. The hydrolysis of proteins usually produces a protein hydrolysate having a molecular weight distribution of approx. 100 Dalton through to several thousand Dalton. Exemplary cationic protein hydrolysates include a basic protein component with a molecular weight of from 100 to 25000 Dalton, such as from 250 to 5000 Dalton. Cationic protein hydrolysates also include quaternated amino acids and the mixtures thereof. The quaternization of protein hydrolysates or amino acids is often carried out by employing quarternary ammonium salts, such as N,N-dimethyl-N-(n-Alkyl)-N-(2-hydroxy-3-chloro-n-propyl)-ammonium halogenides. The cationic protein hydrolysates can also be further derivatized. Typical examples of cationic protein hydrolysates and derivatives include the products commercially available and known under the INCI trade names of: Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/ Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

The percentage weight of exemplary protein hydrolysate(s) relative to the total weight of the hair cleansing agent as contemplated herein is from 0.01 to 3 wt. %, such as from 0.025 to 2 wt. %, for example from 0.05 to 1 wt. %.

Among the suitable vitamins are the following vitamins, provitamins and vitamin precursors, as well as the derivative thereof:

Vitamin A: The group of substances called Vitamin A include retinol (Vitamin $A_1$) and 3,4-didehydroretinol (Vitamin A2). β-carotin is the provitamin of retinal. Vitamin A-components can include Vitamin A-acid and the esters thereof, Vitamin A-aldehyd and Vitamin A-alkohol, as well as the esters thereof, such as palmitate and acetate.

Vitamin B: The Vitamin B Group or Vitamin B complex include

Vitamin $B_1$ (Thiamin)

Vitamin $B_2$ (Riboflavin)

Vitamin $B_3$. The compounds nicotinic acid amide (niacin amide) are often carried under this designation.

Vitamin B5 (pantothenic acid and panthenol). Among this group, panthenol is used in exemplary embodiments. Usable derivatives of panthenol include, in particular, the esters and ethers of panthenol, pantolacton, as well as cationically derivatized panthenols. Specific examples are panthenoltriacetate, panthenolmonoethylether and the monoacetate thereof, as well as cationic panthenol derivatives.

Vitamin $B_6$ (pyridoxine, as well as pyridoxamine and pyridoxal).

Vitamin C (ascorbic acid): exemplary use in the form of palmitic acid ester, glucoside or phosphate and/or in combination with tocopherolene.

Vitamin E (tocopheroles, more particularly α-tocopherole).

Vitamin F: The term "Vitamin F" usually means essential fatty acids, more particularly linoleic acid, linolenic acid and arachidon acid.

Vitamin H: The compound (3aS,4S,6aR)-2-oxohexahydrothienol[3,4-d]-imidazol-4-valeric acid, which has however since taken on the trivial name of biotin, is designated as Vitamin H.

Exemplary vitamins, provitamins and vitamin precursors are from the groups A, B, E and H, such as nicotinic acid amide, biotin, pantolactone and/or panthenol.

In exemplary embodiments, the weight percentage of the vitamins(s), vitamin derivatives(e), and/or the vitamin precursor(s) relative to the total weight of the hair cleansing conditioners as contemplated herein is from 0.001 to 2 wt. %, such as from 0.005 to 1 wt. %, for example from 0.01 to 0.50 wt.-%.

Glycerine can be separately added to the hair cleansing agents as contemplated herein in a quantity of up to 10 wt. % (relative to the total weight of the agent). However, it can also be a component of the aforementioned hydrous-alcoholic carrier.

Despite foregoing the otherwise usual aforementioned thickeners, use of the aforementioned mixtures (A) and (B)—if necessary in combination with (C)—can achieve a viscosity of from 7000 to 12 000 mPas in the conditioning shampoo. The viscosities set by employing (A), (B)—and if necessary (C)—are highly stable over prolonged storage times and temperature fluctuations.

All viscosities were measured at 20° C. using a Brookfield viscometer and Spindle No. 5 at 20 revolutions per minute.

In another embodiment, the conditioning shampoo as contemplated herein has a viscosity of from 7000 to 12 000 mPas (20° C./Brookfield viscometer/Spindle 5/20 rpm).

Other active ingredients, adjuvants and additives, which can be contained in the shampoo as contemplated herein, include:

Plant extracts,

Moisture retaining agents,

Perfumes,

UV filters,

Structurants such as malic acid and lactic acid,

Dyes for coloring the agent,

Substances for setting the pH value, for example α- and β-hydroxycarboxylic acids, such as citric acid, lactic acid, citric acid, glycolic acid, and/or bases, such as alkanolamines and/or sodium hydroxide, Complexing agents such as EDTA, NTA, β-alanindiessig acid and phosphonic acids, Ceramides. Ceramides include N-acylsphingosine (fatty acid amides of sphingosin) or synthetic analogs of such lipids (so-called pseudo-ceramides), Propellants, such as propane-butane mixtures, $N_2O$, dimethylether, $CO_2$ and air, antioxidants, Preservatives, such as sodium benzoate, phenoxyethanol and/or salicylic acid, Examples The following conditioning shampoos have been produced. The quantity values in the tables refer to [wt. %]:

|  | V | E |
|---|---|---|
| Natrium Laureth sulfate (70% hydrous solution) | 12.5 | 12.5 |
| Dinatrium Cocoamphodipropionat | 2.0 | 2.0 |
| Cocoamidopropylbetain (40% hydrous solution) | 4.0 | 4.0 |
| Cocoamid Monoethanolamin | 0.9 | 0.9 |
| Sunflower oil PEG-8 Ester | — | 1.0 |
| Citric acid | 0.5 | 0.5 |
| Sodium benzoate | 0.5 | 0.5 |
| Polyquaternium-10 | 0.3 | 0.3 |
| PEG-40 Hydrogenated Castor Oil | 0.1 | 0.1 |
| Water | ad 100 | ad 100 |
| pH | 4.5-5.0 | 4.5-5.0 |

The shampoos in the example V (comparison) and also the example (present disclosure) were rated on 5 probands each with respect to their conditioning effect. The rating was carried out by trained people (hairdressers), to whom the ingredients of the formulations being tested were unknown. The rating was carried out using a scale from 1 (very poor) to 4 (very good). The mean value was formed from all individual values.

Rating of the Conditioning Effect

|  | V | E |
| --- | --- | --- |
| Grip of the foam in the hair | 1.3 | 2.8 |
| Grip of the hair during rinse-off | 1.5 | 3.6 |
| Disentanglement of the hair | 1.7 | 2.3 |
| Combability of the wet hair | 1.2 | 2.8 |
| Hold of the wet hair | 1.2 | 3.2 |
| Combability of the dry hair | 1.2 | 2.8 |
| Static charging of the dry hair | 1.4 | 3.3 |
| Grip of the dry hair | 1.3 | 4.0 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A conditioning shampoo comprising:

(A) a mixture of the mono-, di- and tri-esters of a fatty acid mixture (F1) and glycerine, and (B) a mixture of the mono- and di-esters of a fatty acid mixture (F1) and a polyethylene glycol having a mean molecular mass of from 200 to 800 g/mol, wherein the fatty acid mixture (F1) is a mixture of fatty acids which has the same fatty acid composition as a plant-based oil, and comprises, relative to the total weight of the fatty acid mixture (F1), from 4.0 to 8.0% by weight of palmitic acid, from 3.0 to 7.0% by weight % of stearic acid, from 14.0 to 39.4% by weight of oleic acid, and 60.0 to 88.0% by weight of linoleic acid, and wherein, the total quantity of all plant-based oils included in the conditioning shampoo which are not the same as the fatty acid mixture (F1) and glycerine, is a value of no more than 0.25 wt. %, and a total quantity of all silicone compounds included in the shampoo is a value of no more than 0.25 wt. %.

2. The conditioning shampoo of claim 1, wherein the mixture (A) of the mono-, di- and tri-esters of the fatty acid mixture (F1) and glycerine further comprises a mixture of the compounds from the groups (A1), (A2) and (A3),

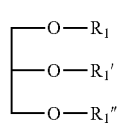
(A1)

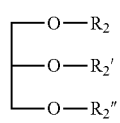
(A2)

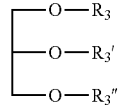
(A3)

wherein in each of the compounds from the group (A1), the radicals R1, R1' and R1" denote, independently of one another, a linear, saturated or mono- or poly-unsaturated $C_8$-$C_{30}$-acyl group, wherein in each of the compounds from the group (A2), one of the radicals from R2, R2' and R2" denotes a hydrogen atom and the other two radicals denote, independently of one another, a linear, saturated or mono- or poly-unsaturated C8-C30-acyl group, and wherein in each of the compounds from the group (A3), two of the radicals from R3, R3' and R3" denotes a hydrogen atom and the third radical denotes a linear, saturated or mono- or poly-unsaturated $C_8$-$C_{30}$-acyl group.

3. The conditioning shampoo of claim 1, wherein mixture (B) of the mono- and di-esters of the fatty acid mixture (F1) and a polyethylene glycol having a mean molecular mass of from 200 to 800 g/mol further comprises a mixture of the compounds from the groups (B1) and (B3),

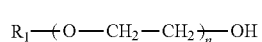
(B1)

(B2)

wherein in each of the compounds from the group (B1), the radical R1 denotes a linear, saturated or mono- or poly-unsaturated $C_8$-$C_{30}$-acyl group, wherein in each of the compounds from the group (B2), the radicals R2, R2' denote, independently of one another, a linear, saturated or mono- or poly-unsaturated $C_8$-$C_{30}$-acyl group, and wherein in each of the compounds from the groups (B1) and (B2), n independently denotes an integer from 1 to 50.

4. The conditioning shampoo of claim 1, wherein the fatty acid mixture (F1) is a mixture of fatty acids, which has the same fatty acid composition as sunflower oil.

5. The conditioning shampoo of claim 1 comprising, relative to the total weight of the conditioning shampoo, the mixtures (A) and (B) in a total quantity [(A)+(B)] of from 0.4 to 3.5 wt. %.

6. The conditioning shampoo of claim 1 wherein the mixtures (A) and (B) are selected from compounds known under the INCI trade name sunflower oil PEG-8 Ester.

7. The conditioning shampoo of claim 1, wherein, relative to the total weight of the conditioning shampoo, the total quantity of all plant-based oils included in the conditioning shampoo, which are not the same as the fatty acid mixture (F1) and glycerine, is a value of maximum 0.20 wt. %.

8. The conditioning shampoo of claim 1, wherein, relative to the total weight of the conditioning shampoo, a total quantity of all silicone compounds included in the conditioning shampoo is a value of maximum 0.20 wt. %.

9. The conditioning shampoo of claim 1 further comprising (C) PEG-40 Hydrogenated Castor Oil, wherein the weight ratio of [(A)+(B)]/(C) is a value from 4.0 to 20.0.

10. The conditioning shampoo of claim 1, wherein, relative to the total weight of the conditioning shampoo, a total quantity of all anionic polymers based on (meth)acrylic acid included in the conditioning shampoo is a value of maximum 0.25 wt. %.

11. The conditioning shampoo of claim 1, wherein, relative to the total weight of the shampoo, a total quantity of sodium chloride included in the conditioning shampoo is a value of maximum 0.25 wt. %.

12. The conditioning shampoo of claim 1, wherein, relative to the total weight of the conditioning agent, a total quantity of all anionic and non-ionic polysaccharides included in the conditioning shampoo is a value of maximum 0.25 wt. %.

13. The conditioning shampoo of claim 1, wherein the conditioning shampoo has a viscosity of from 7000 to 12 000 mPas (20° C./Brookfield viscometer/Spindle 5/20 rpm).

14. The conditioning shampoo of claim 1, wherein mixture (B) of the mono- and di-esters of the fatty acid mixture (F1) and a polyethylene glycol having a mean molecular mass of from 200 to 800 g/mol further comprises a mixture of the compounds from the groups (B1) and (B3),

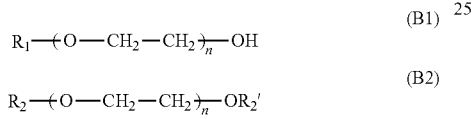

wherein in each of the compounds from the group (B1), the radical R1 denotes a linear, saturated or mono- or poly-unsaturated $C_8$-$C_{30}$-acyl group, wherein in each of the compounds from the group (B2), the radicals R2, R2' denote, independently of one another, a linear, saturated or mono- or poly-unsaturated $C_8$-$C_{30}$-acyl group, and wherein in each of the compounds from the groups (B1) and (B2), n independently denotes an integer from 2 to 40.

15. The conditioning shampoo of claim 1, wherein mixture (B) of the mono- and di-esters of the fatty acid mixture (F1) and a polyethylene glycol having a mean molecular mass of from 200 to 800 g/mol further comprises a mixture of the compounds from the groups (B1) and (B3),

wherein in each of the compounds from the group (B1), the radical R1 denotes a linear, saturated or mono- or poly-unsaturated $C_8$-$C_{30}$-acyl group, wherein in each of the compounds from the group (B2), the radicals R2, R2' denote, independently of one another, a linear, saturated or mono- or poly-unsaturated $C_8$-$C_{30}$-acyl group, and wherein in each of the compounds from the groups (B1) and (B2), n independently denotes an integer from 3 to 30.

16. The conditioning shampoo of claim 1, wherein mixture (B) of the mono- and di-esters of the fatty acid mixture (F1) and a polyethylene glycol having a mean molecular mass of from 200 to 800 g/mol further comprises a mixture of the compounds from the groups (B1) and (B3),

wherein in each of the compounds from the group (B1), the radical R1 denotes a linear, saturated or mono- or poly-unsaturated $C_8$-$C_{30}$-acyl group, wherein in each of the compounds from the group (B2), the radicals R2, R2' denote, independently of one another, a linear, saturated or mono- or poly-unsaturated $C_8$-$C_{30}$-acyl group, and wherein in each of the compounds from the groups (B1) and (B2), n independently denotes an integer from 4 to 20.

17. The conditioning shampoo of claim 1 comprising, relative to the total weight of the conditioning shampoo, the mixtures (A) and (B) in a total quantity [(A)+(B)] of from 0.8 to 1.4 wt. %.

* * * * *